United States Patent [19]

Suga et al.

[11] Patent Number: 4,983,526
[45] Date of Patent: Jan. 8, 1991

[54] METHOD OF MEASURING AND CONTROLLING OZONE CONCENTRATION

[75] Inventors: Shigeru Suga, Tokyo; Kenhachi Mitsuhashi, Kanagawa, both of Japan

[73] Assignees: Suga Test Instruments Co., Ltd.; Yokohama Rubber Co., Ltd., both of Tokyo, Japan

[21] Appl. No.: 314,926

[22] Filed: Feb. 24, 1989

[30] Foreign Application Priority Data

Feb. 26, 1988 [JP] Japan ................................. 63-45164

[51] Int. Cl.$^5$ ...................... G01N 17/00; G01N 21/00
[52] U.S. Cl. ........................................ 436/55; 436/138; 436/171; 436/135; 436/175; 436/73; 436/83; 364/571.01; 364/571.02; 364/571.05; 364/496; 364/497; 364/498; 73/865.6
[58] Field of Search ............... 436/135, 136, 138, 171, 436/5, 55; 422/93, 83 (U.S. only); 73/865.6; 364/571.01, 571.02, 571.05, 496, 500, 497, 498

*Primary Examiner*—Robert J. Hill, Jr.
*Assistant Examiner*—David Redding
*Attorney, Agent, or Firm*—Wenderoth, Lind & Ponack

[57] ABSTRACT

A method of measuring or controlling ozone concentration by ultraviolet ray absorptiometry, includes charging air into a testing tank with its temperature controlled, measuring the disturbing gases generated from testpieces such as rubber samples inside the testing tank by regarding them as ozone, subtracting a value representative of the disturbing gases with a calculation circuit from a value indicative of the preexisting state in the tank to set the ozone concentration at zero, generating a necessary quantity of ozone with an ozonizer by using the zero ozone concentration as a reference point, suspending the generation of ozone after the passage of a predetermined time, measuring once again to obtain a new ozone concentration zero value, adjusting the ozone concentration zero value to the new value if there has been a change in the amount of disturbing gases generated, and repeating at least once the operation described above to regulate the ozone concentration to a desired ozone concentration.

2 Claims, 4 Drawing Sheets

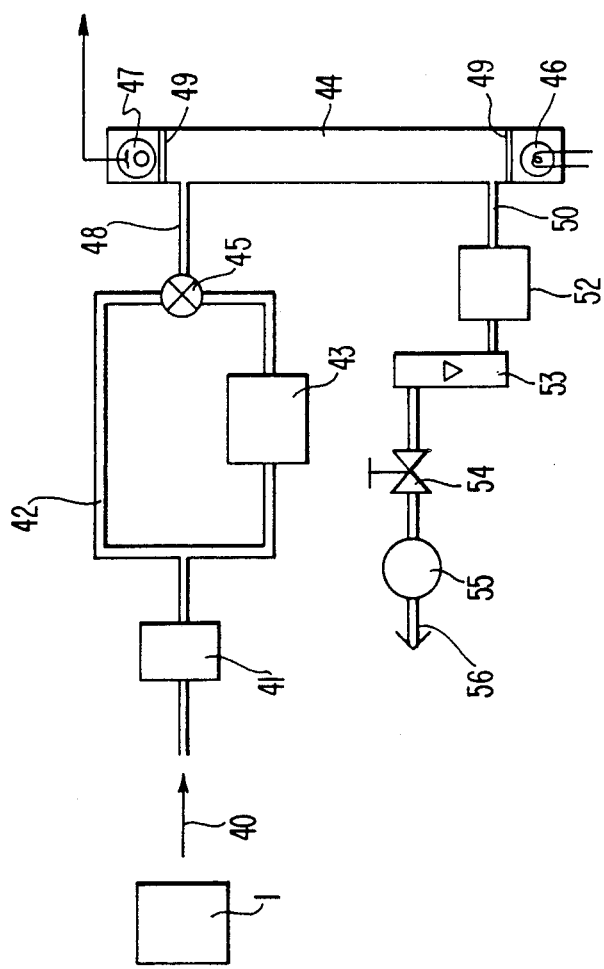

METHOD OF MEASURING AND CONTROLLING OZONE CONCENTRATION

BACKGROUND OF THE INVENTION

1. Field of the Invention

This invention relates to a method of measuring and controlling the concentration of ozone by ultraviolet ray absorptiometry in an ozone weatherometer, which method can artificially promote and test those cracks of rubber products typified by car tires which are generated by ozone in air.

2. Description of the Prior Art

A conventional method of measuring and controlling the concentration of ozone by ultraviolet ray absorptiometry employs an arrangement such as that shown in FIG. 4 of the accompanying drawings, wherein dust of ozonized air 40 entering an ultraviolet ray absorption cell 44 from an ozone testing tank 1 is first removed by a filter 41. Then the ozonized air may enter an ultraviolet ray absorption cell 44 through either a bypass 42 or through a zero-gas filter 43, respectively, depending upon the state of a switching operation.

This switching operation is carried out continuously by automatic change-over valve 45 which effectively switches the path to the cell 44. Ultraviolet rays from a mercury lamp 46 are irradiated through the ultraviolet ray absorption cell 44 and are received by a measuring photo-receiver 47.

Assuming that a photocurrent flowing through the measuring photo-receiver 47 is Io when a gas made ozone-free after passing through the zero-gas filter 43 flows through the ultraviolet ray absorption cell 44, then the difference $\Delta I = Io - Im$ has a proportional relation when the ozone concentration is in the pphm order. Therefore, the ozone concentration is calculated by an electrical calculation circuit which calculates this difference $\Delta I$. And, the concentration is displayed and recorded or merely displayed.

Incidentally, reference numeral 48 in the drawing represents a suction port, 49 a quartz plate, 50 an exhaust port, 52 an exhaust processor, 53 a flow meter, 54 a flow regulating valve, 55 a pump and 56 exhaust.

The problem with the prior art technique described above is as follows. Since the ultraviolet rays (253.7 nm) for measuring ozone are absorbed by a large number of gases of organic solvents, e.g. benzene, acetone, toluene, etc. steam, $SO_2$, and the like, it is an essential condition for the zero-gas filter to absorb and decompose only ozone but not to react at all with other gases in order to facilitate an accurate measurement of ozone concentration.

However, the zero-gas filter unavoidably adsorbs and decomposes the disturbing gases to some extents. In other words, the zero-gas filter decomposes and adsorbs 100% of ozone but at the same time decomposes and adsorbs about 20 to 30% of the disturbing gases, and its reaction with the disturbing gases is not completely zero. Particularly when the number of testpieces placed into the ozone testing tank is large, the disturbing gases such as the gases of the organic solvents occurring from the testpieces are not negligible and if there is any difference between when the disturbing gases pass through the bypass and when they pass through the zero-gas filter, this difference results in an error in the ozone concentration measured.

Ozone concentration measurement by ultraviolet ray absorptiometry has the advantages in that chemicals such as reagents that are required for a chemical analytical method are not all necessary and the measuring procedure is simple, but is not free from the drawback of the measurement error occurring due to the disturbing gases.

In accordance with the prior art method described above the measurement is carried out on the premise that any influence of the disturbing gases can be neglected, but the occurrence of the disturbing gases cannot be neglected on the number of testpieces, the difference of their material, the testing temperature, and so forth.

If the site of installation of the tester is the production site of rubber products, various organic matters are emitted during the production process carried out at the site and the air itself sucked into the testing tank contains large quantities of disturbing gases.

Therefore, when the ozone concentration of the testing tank is about 50 pphm, the disturbing gases sometime account for about 20 to 30% and in the case of automatic control, the ozone concentration inclusive of the disturbing gases is controlled as the ozone concentration, though the ozone value is substantially 80 to 70%. In the case of using an ozone concentration of 50 pphm, 40 to 35 pphm is the real ozone concentration and 20 to 15 pphm is sometimes a false ozone concentration due to the disturbing gases.

Even though the ozone concentration is apparently adjusted to 50 pphm, its value fluctuates so that the test results become different and judgement becomes difficult from time to time.

Accordingly, it has become necessary to eliminate in advance the disturbing gases such as the organic solvent gases which may be measured erroneously as ozone contained in air, to identify accurately the disturbing gases generated from the testpiece and to measure and control the concentration of ozone based on a value from which an influence of the disturbing gas component is eliminated.

SUMMARY OF THE INVENTION

In view of the problems with the prior art technique described above, the present invention has as its object to provide an ozone concentration measurement/control method which eliminates in advance any disturbing gases which would be measured erroneously as ozone contained in air, identifies accurately the disturbing gases generated from testpieces such as rubber samples in the testing tank, measures and controls the ozone concentration based on a value free from an adverse influence of the disturbing gas component and can facilitate the ozone concentration test in an accurate ozone concentration atmosphere.

To eliminate the problems of the prior art, the present invention employs the following means.

In an ozone concentration measurement/control method using ultraviolet ray absorptiometry, the present invention comprises the steps of controlling air temperature, sending the air into the testing tank, measuring the disturbing gases generated from the testpiece such as a rubber sample in the testing tank by regarding the gases as indicative of ozone, subtracting this measured value with a calculation circuit so as to make an ozone concentration zero, generating necessary ozone by an ozonizer using the above as a reference point, suspending the generation of ozone after the passage of a predetermined time, measuring once again to obtain a new ozone concentration zero value using the technique described above, adjusting the ozone concentration zero value to the new value if there has been a change in the generated quantity of the disturbing gases, repeating the procedures described above at least once to regulate the ozone concentration to a desired ozone concentration.

Initially in the ozone concentration test, the sample is brought into a thermostatic state and the disturbing gases generated from the sample are measured by regarding them as ozone. This measured value is used as an initial reference ozone concentration zero value.

Air purified by a disturbing gas removing filter is charged into an ozonizer so that the interior of a testing tank reaches a required ozone concentration of zero value as the reference, and the photo-energy of an ozone lamp inside the ozonizer, for example, is controlled in order to control the ozone generation and to supply the ozone into the testing tank.

The supply of air into the ozonizer is suspended after the passage of a predetermined time and a new air path is selected by interlocking change-over valves. The air inside the testing tank is replaced with air bypassing the ozonizer and the ozone concentration is made zero. Under this state, the disturbing gases in the air inside the testing tank are measured by regarding them as ozone in the same way as described above. This value is used as a new ozone concentration zero value and the previous ozone concentration is cancelled.

The air path is then selected by the interlocking change-over valves to again flow through the ozonizer and ozone is generated by this ozonizer so that the ozone concentration in the testing tank 1 attains a predetermined concentration by use of the second ozone concentration zero value as a reference.

The procedure described above are repeated at least once and the test under the accurate ozone concentration free from any adverse influences of the disturbing gases can now be carried out.

The above and other objects and novel features of the present invention will become more apparent from the following description when taken in conjunction with the accompanying drawings.

BRIEF DESCRIPTION OF THE DRAWINGS

FIG. 4 is a schematic diagram of an apparatus for measuring and controlling the concentration of ozone according to the prior art.

DETAILED DESCRIPTION OF THE PREFERRED EMBODIMENTS

Figure 1:
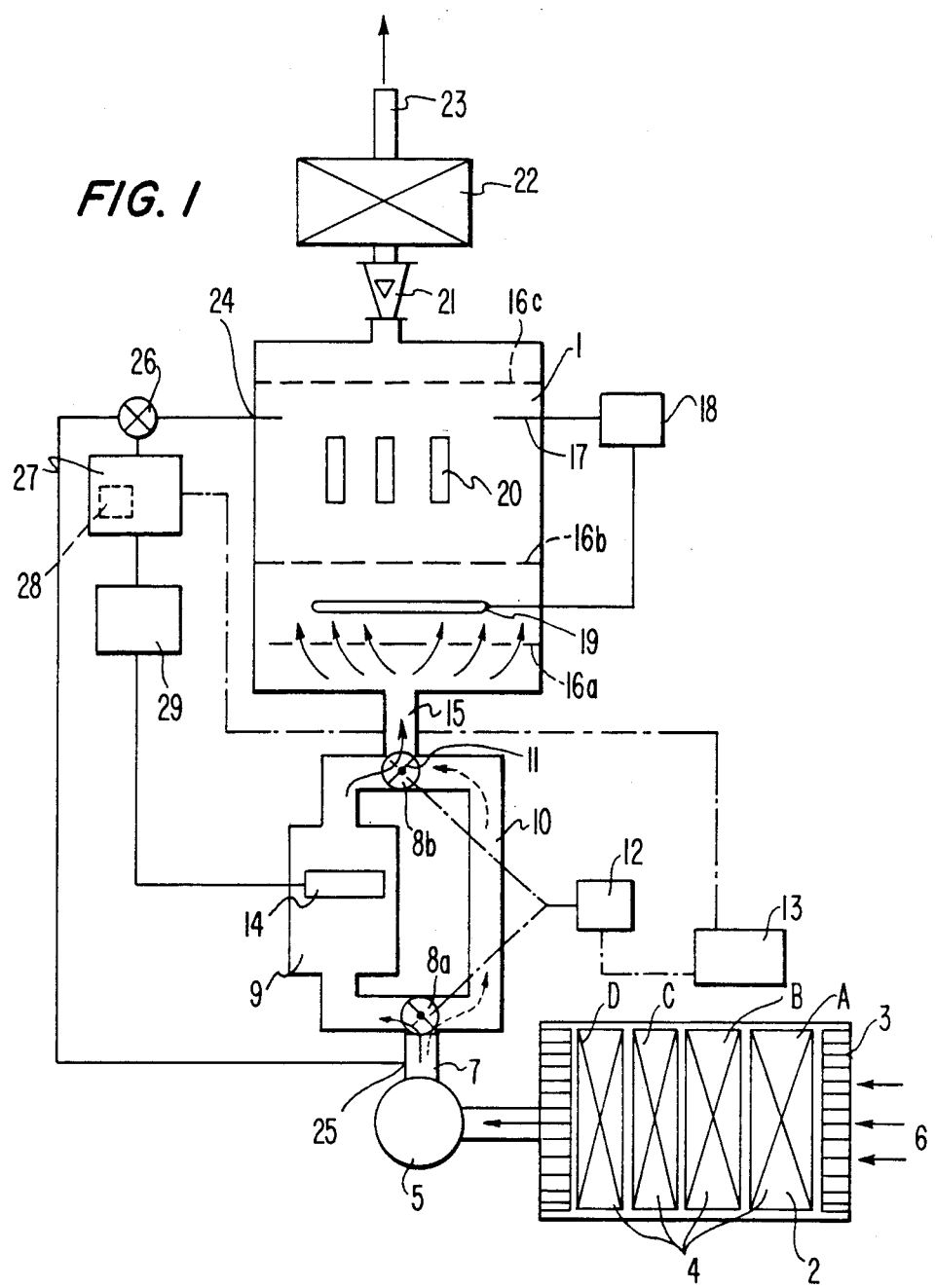
FIGS. 1, 2 and 3 are schematic diagrams of an apparatus for measuring and controlling the concentration of ozone according to the present invention.

Hereinafter, an embodiment of the present invention will be described with reference to the accompanying drawings.

The intake of air into a testing tank 1 is first made through a disturbing gas removing filter 2. This filter 2 consists of a plurality of layers of disturbing gas removing agent 4 including a dusting filter 3, a disturbing gas removing agent A (strong oxidizing agent), a disturbing gas removing agent B (neutral adsorbent), a disturbing gas removing agent C (catalytic adsorbent) and a disturbing gas removing agent D (physical adsorbent). This disturbing gas removing filter 2 may consist of the disturbing gas removing agent or of a combination of the above-mentioned disturbing gas removing agents.

While the external air 6 sucked by a blower 5 passes through the disturbing gas removing filter 2, the dust in the external air is removed by the dusting filter 3 and odoring substances undergo an oxidation reaction with the strong oxidizing agent and are fixed as oxides. The acidic gas or alkaline gas is neutralized and removed by the neutral adsorbent and oxidants and the like are treated by the catalytic adsorbent. Organic solvent gases are adsorbed by the physical adsorbent. In this manner the external air is purified by the disturbing gas removing agents according to their peculiar characteristics.

The purified air passes through the air passage 7 and flows either through the ozonizer 9 or through a bypass 10 depending upon the position of an interlocking change-over valve 8a.

The ozonizer 9 and the bypass 10 are branched from each other and another interlocking change-over valve 8b is disposed at the outlet of their confluence. The interlocking change-over valves 8a, 8b open the ozonizer 9 when valve mechanisms of change-over valves 8a, 8b are at the positions represented by a solid line and open the bypass 10 when the valve mechanisms 11 are at the positions represented by a dashed line in the drawing.

The same function of switching can be accomplished by eliminating the bypass 10 and turning ON and OFF the ozonizer 9.

The valve mechanisms 11 of the interlocking change-over valves 8a, 8b are operated by a change-over valve operator 12 and a time control system 13.

An ozone lamp 14 as means for generating ozone is disposed inside the ozonizer 9 and ozonizes the air flowing inside the ozonizer 9.

The ozonizer air leaving the ozonizer 9 or the purified air passing through the bypass 10 enters the testing tank 1 at its bottom through an air passage 15.

The ozonized air (or purified air) is diffused by a sheet-like diffusion plate 16a having a large number of perforations, is heated by a heater 19 which is controlled by a temperature-sensor 17 and a temperature regulator 18, is further diffused y a diffusion plate 16b, flows inside the tank and comes into contact with a testpiece 20.

The ozonized air (or purified air) then flows through a diffusion plate 16c, a flow meter 21 and an exhaust processor 22 and is discharged outside via an exhaust port 23.

Control of the concentration inside the testing tank 1 is carried out in the following way. Air inside the tank collected from an ozone collection port 24 and purified air collected from a zero-gas collection port 25 (hereinafter referred to as "zero-gas") in the air passage 7 are charged alternately into an ozone concentration measuring instrument 27 by a change-over valve 26, and such air is compared to control the photo-energy of the ozone lamp 14 by means of a controller 29.

The measurement/control method of measuring/controlling the ozone concentration will be next described in detail.

Figure 2:
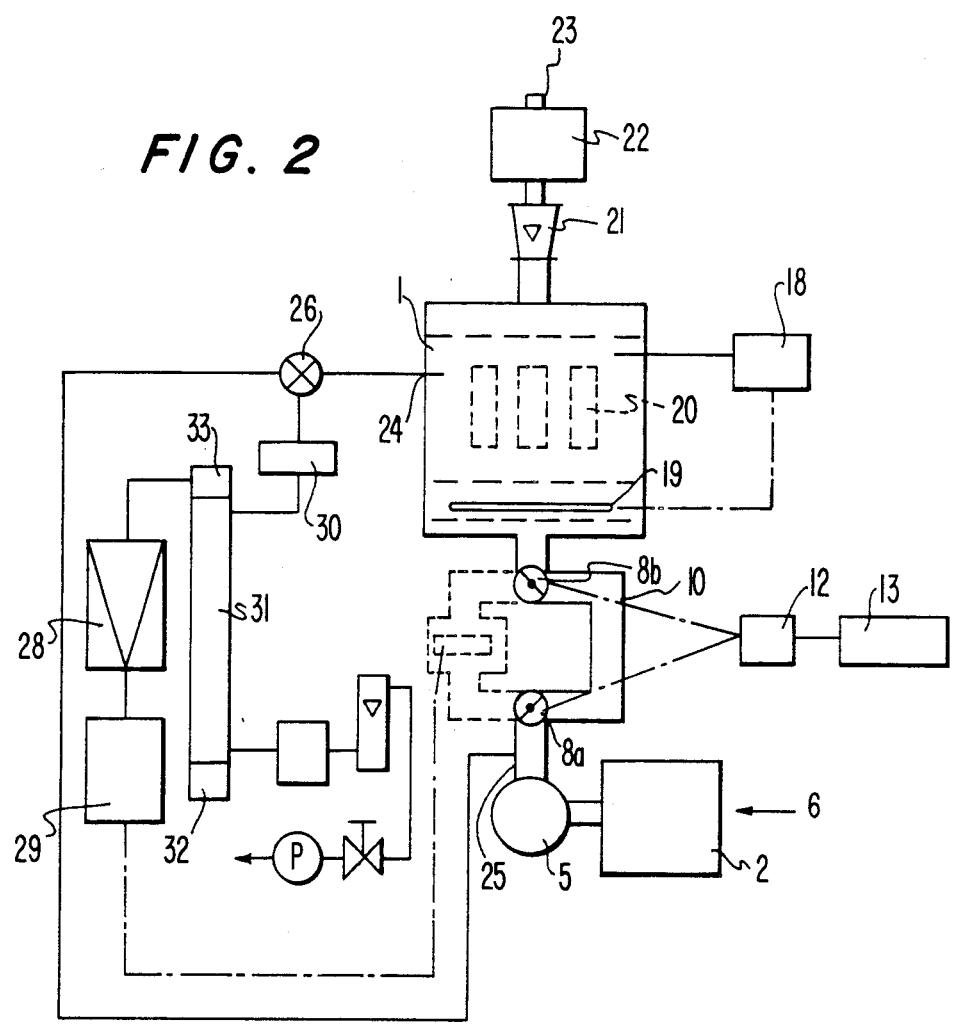

FIG. 2 shows the mode of the flow of the external air 6. A change-over valve operator 12 operates upon receiving an instruction from a time control system 13, the interlocking change-over valves 8a, 8b open the bypass air passage 10 and the external air 6 is rendered to zero-gas by the disturbing gas removing filter 2. The zero-gas is formed through the bypass 10 by the blower 5, is sent into the testing tank 1, is controlled to a predetermined temperature by the heater 19 and is discharged to the outside through the flow meter 21, the exhaust processor 22 and the exhaust port 23.

If no testpiece 20 exists under this state, the change-over valve 26 is set to the ozone collection port side 24 to collect the gas in the testing tank 1, and the gas is caused to flow through an ultraviolet ray absorption cell 31 via a filter 30. Ultraviolet rays from a mercury lamp 32 are irradiated toward a photo-receiver 33 and a photo-current measured by photo-receiver 33 is set to io.

When the change-over valve 26 is switched and the zero-gas is collected from the zero-gas collection port 25, the photo-current is also io because the gas is the zero-gas, and there is no difference between these photo-currents.

An amplification calculation circuit 28 makes a calculation and displays a result from the calculation on the premise that the ozone concentration is zero.

Next, the case where the testpiece 20 is disposed in tank 1 will be considered. The rubber sample is exposed to the heated air and trace amounts of oil, an age-resistor, a vulcanization promotor, etc, in the rubber sample are vaporized and mix into the air inside the tank. If the air inside the tank is measured in this case, those gases which are not ozone but which absorb the ultraviolet rays irradiated by mercury lamp 33 (253.7 nm) (hereinafter referred to as the "disturbing gases") would be measured erroneously as ozone.

In other words, if the photo-current generated by the collection of the gas sampled from the testing tank is id and the photo-current due to the zero-gas is io, the difference $\Delta i = io - id$ is generated when $io > id$ and is calculated and displayed as ozone.

Under the state shown in FIG. 2, the ozone concentration should be originally zero and so, $-\Delta i$ is added by using an electrical circuit and the ozone concentration is calculated and displayed as zero.

In other words, under the state where the zero-gas passes through the bypass 10, the amplification calculation circuit operates in such as manner that the ozone concentration is always zero. Ozone concentration control is effected with this zero value as a reference.

Figure 3:
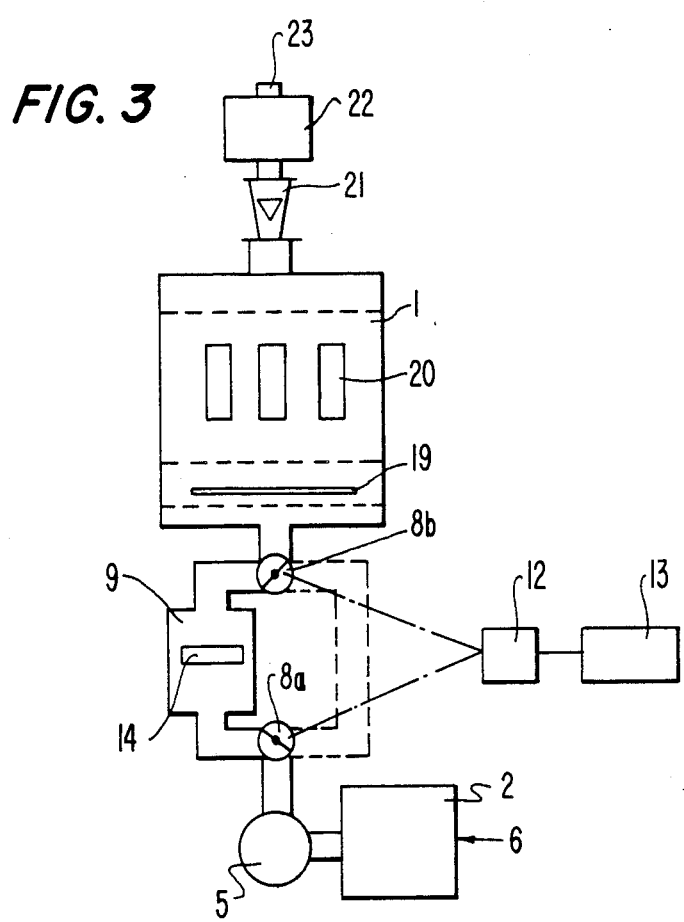

FIG. 3 shows a state where the interlocking change-over valves 8a, 8b are opened to define a path through the ozonizer 9 by a signal from a time control system 13.

The zero-gas passing through the disturbing gas removing filter 2 is converted to ozonized air by the ozone lamp 14 inside the ozonizer 9 and enters the testing tank 1.

The ozonized air heated by the heater 19 comes into contact with the testpiece 20 inside the tank and a degradation of the testpiece 20 due to the ozone proceeds.

Ultraviolet absorption from the mercury lamp 32 occurs inside the ultraviolet ray adsorption cell 31 due to the ozonized air inside the testing tank 1 collected by controlling the change-over valve 26 to open the ozone collection port 24 to cell 31, and the photo-current measured in the photo-receiver 33 becomes ioz. In comparison with the photo-current io generated by the zero-gas collected by controlling the change-over valve 26 to open the zero-gas collection port 25 to cell 31, there is the relation $io > ioz$ and the difference $\Delta i' = io - ioz$ is proportional to the ozone concentration.

This $\Delta i'$ value is calculated by the amplification calculation circuit and is displayed as the ozone concentration. The controller 29 is operated so that the value reaches a predetermined concentration to control the photo-energy of the ozone lamp 14. In this manner the ozone concentration can be controlled accurately.

After the passage of a predetermined period of time (e.g. 4 hours), this state is switched to a state where the interlocking change-over valves 8a, 8b open the bypass 10 by receiving a signal from the time control system 13, and the ozonized air inside the testing tank 1 is replaced with zero-gas.

The photo-current when substitution is completed is id' and its difference from the photo-current io' when the change-over valve 26 is in the zero-gas collection mode, that is, $\Delta i'' = io' - id'$, results from the disturbing gas. If this value $\Delta i''$ is compared with $\Delta i$ that was previously measured as an indication of the disturbing gases and if $\Delta i > \Delta i''$, the inequality means that there is a difference in the disturbing gas generation quantity. Accordingly, the aforementioned calculation of making the ozone concentration zero by adding $-\Delta i$ is cancelled and a new calculation for making the ozone concentration zero is carried out by adding the new value $-\Delta i''$.

The experiments carried out by the present inventors reveal that when 40 testpieces were placed into the testing tank at a temperature of 40° C. and an ozone concentration of zero, 5 to 7 pphm of disturbing ozone was generated from the testpieces, though depending on the kind of testpieces, the condition was stabilized within about 30 minutes. This disturbing gas was stabilized 3 hours after the start of the test and did not change much up to 96 hours after completion of the test. Four hours after the start of the test, the ozone lamp was turned off to make the amount of ozone in the testing tank zero. About 6 minutes was necessary for this and the ozone concentration 6 minutes later was used as the disturbing gas generation quantity and as a new ozone concentration zero. One minute was necessary for this purpose. Thereafter about 6 minutes was necessary to raise the ozone concentration to a set concentration. A cessation of the test for 13 minutes in total could provide a correct ozone concentration test and did not affect the total test time of 96 hours.

Thereafter, the operations described above were repeated or in other words, the generation quantity of the disturbing gas was checked at predetermined intervals as the ozone concentration, followed then by the subtraction by the amplification calculation circuit to make the ozone concentration zero. Using this value as a reference, an ozone concentration was controlled to a predetermined ozone concentration, e.g. 50 pphm, and a test with a substantial ozone concentration was carried out for a predetermined period.

If the disturbing gas does not exhibit any change with the passage of the testing time and a constant generation quantity is obvious, the ozone concentration zero value adjustment may be made only once at the initial stage. Thereafter, the ozone concentration test can be carried out continuously without being interrupted by the ozone concentration zero value adjustment described above. Such a method is also embraced within the scope of the present invention.

Incidentally, the total amount of the disturbing gas in air and the disturbing gas generated from the testpiece can be identified accurately and the control of ozone concentration carried out after accounting for such.

Correction of the ozone concentration zero value can be made with the disturbing gas remaining in the air. This is the case where the intake air is stable and in such a case, a filter for removing various disturbing gases is not necessary and only a filter for removing dust in the air may be needed.

As described above, the method of the present invention eliminates in advance those disturbing gases which might be erroneously measured as ozone contained in air, such as organic solvent gases, identifies accurately the disturbing gases generated from the testpiece and measures and controls an ozone concentration based on a value from which the disturbing gas component is removed.

In other words, while the prior art method regards the disturbing gas as ozone and tests the ozone concentration including the disturbing gas, the method of the present invention makes it possible to make an accurate test with real ozone concentration free from the adverse influence of the disturbing gas.

In accordance with the conventional concentration measurement method, the generated quantity of the disturbing gas differs depending on the number of testpieces put at one time into the testing tank. Therefore, even if an apparent ozone concentration is the same, an actual ozone concentration is different. Accordingly, the time required until cracks occur in the testpiece is non-uniform and problems are likely to occur in the judgement of the worthiness of products. The method of the present invention eliminates such problems because the test results are uniform.

(EXAMPLES)

Sample dimension: 10 mm wide×60 mm long×2 mm thick

Stretch ratio: 20%

Temperature: 40°±1° C.

Ozone concentration: 50±5 pphm (the prior art method and the method of the present invention are used for measurement).

| Kind of samples | Number of samples in testing tank | Testing time until the occurrence of cracks Ozone concentration | |
|---|---|---|---|
| | | By prior art method | By method of this invention |
| Rubber sample A | 30 | 7 ± 1 hr | 5 ± 0.5 hr |
| Rubber sample A | 100 | 18 ± 3 hr | 5 ± 0.5 hr |
| Rubber sample B | 30 | 5 ± 1.0 hr | 3.5 ± 0.5 hr |
| Rubber sample B | 100 | 10 ± 1 hr | 3.5 ± 0.5 hr |

Conventionally, a problem between a manufacturer of rubber products and users sometime resulted in the discarding of the products themselves and the economic loss was extremely great. However, the present invention can eliminate such a problem.

Although the present invention has thus been described with reference to one preferred embodiment, the invention is not particularly limited thereto but can be changed or modified in various manners without departing from the scope and spirit thereof.

What is claimed is:

1. A method of measuring or controlling a concentration of ozone by ultraviolet ray absorptiometry, said method comprising:
   charging air into a testing tank and controlling the temperature of the air charged into the tank;
   measuring any disturbing gases generated from testpieces such as rubber samples inside the testing tank by regarding any disturbing gases as ozone;
   subtracting a value representative of the quantity of any disturbing gases regarded as ozone, by using a calculation circuit, from a value representative of a preexisting state in the testing tank to obtain a value representative of the ozone concentration in the testing tank being zero;
   generating a necessary quantity of ozone in the tank with an ozonizer by using the value representative of the ozone concentration being zero as a reference point;
   suspending the generation of ozone after the passage of a predetermined time;
   obtaining a new said value representative of the ozone concentration being zero;
   adjusting the value representative of the ozone concentration being zero, which is used in the step of generating, to said new value if there has been a change in the amount of disturbing gases generated since the step of measuring was carried out; and
   repeating at least once the above steps to regulate the ozone concentration to a desired ozone concentration.

2. A method of measuring or controlling the ozone concentration according to claim 1, further comprising removing disturbing gases, which would be recognized erroneously and measured as ozone from the air before being charged into the testing tank, with a disturbing gas removing filter comprising disturbing gas removing agents selected from the group consisting of a strong oxidizing agent, a neutral adsorbent, a catalytic adsorbent and a physical adsorbent, either alone or in combination.

* * * * *